United States Patent
Destaillats et al.

(10) Patent No.: US 9,826,767 B2
(45) Date of Patent: *Nov. 28, 2017

(54) INFANT FORMULA WITH A LOW CONTENT OF MCFAS IN SPECIFIC PROPORTIONS AND A RELATIVELY HIGH CONTENT OF UNSATURATED FATTY ACIDS, AND ITS USE IN PROMOTING THE HEALTHY ESTABLISHMENT OF COGNITIVE FUNCTION IN INFANTS

(71) Applicant: NESTEC S.A., Vevey (CH)

(72) Inventors: Frederic Destaillats, Servion (CH); Kornel Nagy, Lausanne (CH); Sagar Thakkar, Brent (CH)

(73) Assignee: Nestec S.A., Vevey (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/780,239

(22) PCT Filed: Apr. 2, 2014

(86) PCT No.: PCT/EP2014/056582
§ 371 (c)(1),
(2) Date: Sep. 25, 2015

(87) PCT Pub. No.: WO2014/166790
PCT Pub. Date: Oct. 16, 2014

(65) Prior Publication Data
US 2016/0037818 A1    Feb. 11, 2016

(30) Foreign Application Priority Data

Apr. 10, 2013 (EP) ..................... 13163186

(51) Int. Cl.
| | | |
|---|---|---|
| *A61K 31/19* | (2006.01) |
| *A61K 31/20* | (2006.01) |
| *A23L 1/29* | (2006.01) |
| *A23L 1/30* | (2006.01) |
| *A61K 31/202* | (2006.01) |
| *A23L 33/00* | (2016.01) |
| *A23L 33/115* | (2016.01) |
| *A23L 33/12* | (2016.01) |

(52) U.S. Cl.
CPC ........... *A23L 1/3008* (2013.01); *A23L 33/115* (2016.08); *A23L 33/12* (2016.08); *A23L 33/40* (2016.08); *A61K 31/19* (2013.01); *A61K 31/20* (2013.01); *A61K 31/202* (2013.01); *A23V 2002/00* (2013.01); *A23V 2200/30* (2013.01); *A23V 2200/322* (2013.01)

(58) Field of Classification Search
CPC ........ A23L 33/12; A23L 33/115; A23L 33/40; A61K 31/19; A61K 31/20; A61K 31/202; A23V 2002/00; A23V 2200/30; A23V 2200/322

See application file for complete search history.

(56) References Cited

U.S. PATENT DOCUMENTS

| | | |
|---|---|---|
| 5,709,888 A | 1/1998 | Gil et al. |
| 6,034,130 A | 3/2000 | Wang et al. |
| 2002/0045660 A1 | 4/2002 | O'Connor et al. |
| 2010/0234286 A1 | 9/2010 | Georgi et al. |
| 2012/0121757 A1 | 5/2012 | Zwijsen et al. |

OTHER PUBLICATIONS

Carnielli et al. "Medium-chain triacylglycerols in formulas for preterm infants: effect on plasma lipids, circulating concentrations of medium-chain fatty acids, and essential fatty acids1-3" The American Journal of Clinical Nutrition, 1996, vol. 64, pp. 152-158, XP009171933.
Innis et al. "Docosahexaenoic acid and arachidonic acid enhance growth with no adverse effects in preterm infants fed formula" The Journal of Pediatrics, May 2002, pp. 547-554.
Jorgensen et al. "Fatty acid composition in Danish infant formula compared to human milk" Scandinavian of Journal Nutrition Naringsforskning, 1995, vol. 39, pp. 50-54.
Ramirez et al. "Plasma and red blood cell fatty acid composition in small for gestational age term infants fed human milk or formula" Clinical Nutrition, 1998, vol. 17, pp. 177-183.
Wu et al. "Production Technology of Dairy Products" China Light Industry Press, Jan. 2001, p. 275, 6 pages.
Chinese Office Action for Application No. 201480020459.6, dated Jun. 1, 2017 (26 pages).

*Primary Examiner* — Sahar Javanmard
(74) *Attorney, Agent, or Firm* — K&L Gates LLP

(57) ABSTRACT

The invention concerns a synthetic infant formula composition with a low content of medium-chain fatty acids in specific proportions and a relatively high content of unsaturated fatty acids, preferably polyunsaturated fatty acids. This composition is for infants, preferably preterm infants. This composition has been designed to promote the healthy establishment of cognitive function.

9 Claims, No Drawings

INFANT FORMULA WITH A LOW CONTENT OF MCFAS IN SPECIFIC PROPORTIONS AND A RELATIVELY HIGH CONTENT OF UNSATURATED FATTY ACIDS, AND ITS USE IN PROMOTING THE HEALTHY ESTABLISHMENT OF COGNITIVE FUNCTION IN INFANTS

CROSS REFERENCE TO RELATED APPLICATIONS

The present application is a National Stage of International Application No. PCT/EP2014/056582, filed on Apr. 2, 2014, which claims priority to European Patent Application No. 13163186.3, filed on Apr. 10, 2013, the entire contents of which are being incorporated herein by reference.

TECHNICAL FIELD

This invention relates to a synthetic infant formula composition with a low content of medium-chain fatty acids (MCFAs) in specific proportions and a relatively high content of unsaturated fatty acids, preferably polyunsaturated fatty acids (PUFAs), and its use in promoting the healthy establishment of cognitive function in infants, preferably in preterm infants.

BACKGROUND OF THE INVENTION

A well-nourished mother's breast milk is universally considered to be the optimum nutrition for healthy full term infants during the first months of life. However all infants cannot be breast fed. Furthermore, the needs of more vulnerable infants such as preterm infants cannot be achieved by their mother's milk. The synthetic infant formulas are therefore of high interest.

Lipid comprise an important part of infant formulas since they provide approximately half of the energy content, they are a source of n-3 and n-6 essential fatty acids and they are necessary for the intestinal absorption of fat-soluble vitamins. The total fat in infant formulas usually comprises 90 to 96 wt % of fatty acids (Golay et al. Journal o AOAC International, Vol 92, No 5, 2009). More recently the nutritional importance of the long-chain polyunsaturated fatty acids with C20 and C22 carbon atoms (LC-PUFAs) in infant formulas has been appreciated.

The efficiency of intestinal absorption of fatty acids from infant formulas is a vital property of the fat blend. As a general principle, short-chain fatty acids are better absorbed than longer chain fatty acids, and unsaturated fatty acids are better absorbed than saturated fatty acids of the same chain length.

In order to achieve good fat absorption similar to that in human milk, infant formulas usually contain a high proportion of vegetable oils.

Medium-chain triacylglycerols (MCTs) are usually manufactured by refining vegetable oils rich in MCFAs, and they have been widely used in infant formulas till today.

The only recommendation of the European Regulations for using these MCTs in infant formulas is that lauric acid (C12:0) and myristic acid (C14:0) are to be provided, separately or as a whole, in a range of from 0 to 20% of the total fat content (Commission Directive 2006/141/EC of 22 Dec. 2006 on infant formulae and follow-on formulae).

U.S. Pat. No. 5,000,975 describes infant formula compositions in which the fat is issued from vegetable oil fat compositions. For preterm and low birth weight infants, MCTs are included in the composition in a total amount of 10 to 25 wt % with respect to the total fat. These MCTs are made up of a mixture of C6:0 (1 to 2%), C8:0 (65 to 75%), C10:0 (25 to 35%) and C12:0 (1 to 2%) fatty acids, derived from coconut oil. These MCTs comprise predominantly C8:0 and C10:0 fatty acids, in amounts of 60-70% of caprylic acid and of 25-35% of capric acid.

More recently, U.S. Pat. No. 5,709,888 describes fat mixtures, in particular for infant nutrition, comprising between about 4.8 to about 28.7% by weight of MCTs in total, with respect to the total fat. In some examples where the total amount of MCTs is of 7.85 to 8.0 wt %, with respect to the total fat, the amount of caprylic acid (C8:0) is around 2.35 to 2.50 wt %, the amount of capric acid (C10:0) is of 3.60 to 3.80 wt % and the amount of lauric acid (C12:0) is of 1.80 to 2.00 wt %, with respect to the total fat.

However the resultant fatty acid pattern is still distinctly different from human milk fat, which represents generally the gold standard in terms of nutrition.

Moreover, it is known that nutrition plays an important role in neuronal maturation in the brain (reviewed in Huppi, P. S. (2008); Nutrition for the Brain, Pediatric Research, 63(3): 229-233.). Specifically, clinical studies have shown that essential fatty acids are crucial to ensure foetal and postnatal brain development (Chang, C. Y. et al. (2009); Essential fatty acids and human brain, Acta Neurol. Taiwan, 18(4): 231-41; Alessandri, J. M. et al. (2004); Polyunsaturated fatty acids in the central nervous system: evolution of concepts and nutritional implications throughout life, Reprod. Nutr. Dev., 44(6): 509-38).

Thus, oral interventions are an appropriate way to positively impact on the development of the nervous system, so as to promote the healthy establishment of cognitive function and mental performance in infants.

There is a need to provide nutritional interventions that meet the nutritional needs of infants.

There is a need to provide compositions that promote and support the healthy establishment of cognitive function, during the early phases of newborn life, when the nervous system is rapidly maturing.

The present inventors have designed synthetic nutritional compositions that are especially adapted to meet the needs of infants. The compositions of the present invention have been designed to ensure the healthy establishment of cognitive function.

It is therefore an object of the invention to provide a synthetic infant formula useful as an alternative for infants, in particular preterm infants, and particularly well adapted for its use in ensuring the healthy establishment of cognitive function in infants.

SUMMARY OF THE INVENTION

The present inventors have found surprisingly that the administration of a low content of MCFAs in specific proportions, together with the administration with of a relatively high content of unsaturated fatty acids, preferably PUFAs, is particularly effective for ensuring the healthy establishment of cognitive function in infants, in particular in preterm infants.

Accordingly, in a first aspect of the invention, there is provided a synthetic infant formula composition comprising:
  medium-chain fatty acids, in the form of triglycerides, in a total amount in the range of 2 to 10 wt %, preferably in the range of 4.5 to 8 wt %;

caproic acid in an amount in the range of 0.6 to 1.3 wt %, preferably in the range of 0.7 to 1.1 wt %, more preferably in the range of 0.8 to 1.0 wt %;

caprylic acid in an amount in the range of 0.8 to 1.5 wt %, preferably in the range of 0.9 to 1.2 wt %, more preferably in the range of 1.0 to 1.1 wt %;

capric acid in an amount in the range of 1.4 to 1.9 wt %, preferably in the range of 1.5 to 1.8 wt %, more preferably in the range of 1.6 to 1.7 wt %; and lauric acid in an amount in the range of 4.0 to 6.0 wt %, preferably in the range of 4.5 to 5.9 wt %, more preferably in the range of 4.5 to 5.5 wt %; and at least one unsaturated fatty acid, preferably at least one polyunsaturated fatty acid (PUFA), the unsaturated fatty acid(s) being present in an amount generally of at least 15 wt %, preferably at least 20 wt %, with respect to the total fatty acids.

The composition is preferably a preterm infant formula.

Surprisingly, the relative low amount of MCFAs in the infant formula according to the invention, in comparison with the infant formulas of the prior art, as well as a new dosage of the medium-chain fatty acids in the form of MCTs, as well as the relatively high amount of unsaturated fatty acids in the infant formula according to the invention, lead to an infant formula which ensures the healthy establishment of cognitive function in infants, in particular in preterm infants.

Thus the nutrients of the composition of the invention are especially associated with brain maturation, especially the development of cognitive function, in infants.

Thus, in a second aspect of the invention, this composition is provided for ensuring the healthy establishment of cognitive function in infants, in particular in preterm infants.

DETAILED DESCRIPTION OF THE INVENTION

For a complete understanding of the present invention and the advantages thereof, reference is made to the following detailed description of the invention.

It should be appreciated that various embodiments of the present invention can be combined with other embodiments of the invention and are merely illustrative of the specific ways to make and use the invention, and do not limit the scope of the invention when taken into consideration with the claims and the following detailed description.

In the present description, the following words are given a definition that should be taken into account when reading and interpreting the description, examples and claims.

As used herein, the following terms have the following meanings.

According to the Commission Directive 2006/141/EC of 22 Dec. 2006 on infant formulae and follow-on formulae, article 1.2 (a), the term "infant" means child under the age of 12 months.

The term "preterm infant" (or "premature infant") means an infant born at least than 37 weeks gestational age.

The term "low birth weight infant" means an infant having a live born weight less than 2,500 g.

The term "infant formula" means a composition as foodstuff intended for particular nutritional use by infants during the first months of life and satisfying by itself the nutritional requirements of this category of person (according to the Commission Directive 2006/141/EC of 22 Dec. 2006 on infant formulae and follow-on formulae, article 1.2 (c)). It has to be understood that infants can be fed solely with infant formulas, or that the infant formula can be used as a complement of human milk. It is synonymous to the widely used expression "starter formula".

According to the Commission Directive 2006/141/EC of 22 Dec. 2006 on infant formulae and follow-on formulae, article 1.2 (d), the term "follow-on formulae" means foodstuffs intended for particular nutritional use by infants when appropriate complementary feeding is introduced and constituting the principal liquid element in a progressively diversified diet of this category of persons.

The term "growing-up milk" means a milk-based nutritional composition.

The term "human milk fortifier" means a nutritional composition for infants intended to be added to or diluted with human milk.

The term "hypoallergenic composition" means a composition which is unlikely to cause allergic reactions.

The term "allergy" means an allergy which has been detected by a medical doctor and which can be treated occasionally or in a more durable manner. The term "food allergy" means an allergy with respect to a nutritional composition.

The term "sialylated oligosaccharide" means an oligosaccharide having a sialic acid residue.

The term "prebiotic" means non-digestible carbohydrates that beneficially affect the host by selectively stimulating the growth and/or the activity of healthy bacteria such as bifidobacteria in the colon of humans (Gibson G R, Roberfroid M B. Dietary modulation of the human colonic microbiota: introducing the concept of prebiotics. J Nutr. 1995; 125:1401-12).

The term "probiotic" means microbial cell preparations or components of microbial cells with a beneficial effect on the health or well-being of the host (Salminen S, Ouwehand A. Benno Y. et al. "Probiotics: how should they be defined" Trends Food Sci. Technol. 1999:10 107-10).

The term "nutritional" means that it nourishes a subject. This infant formula is a nutritional composition, usually to be taken orally, intragastrically, or intravenously, and usually including a lipid or fat source and a protein source.

The term "preterm infant formula" means an infant formula intended for a preterm infant.

The terms "ensuring the healthy establishment of cognitive function" means that the cognitive function of the infant, as measured by a standard method, is in the normal range.

Standard methods known to the skilled person are the Bayley Scales of Infant and Toddler Development® (currently Third Edition (Bayley-III)). This test includes cognitive, language, motor, social-emotional and general adaptive features. Raw scores of successfully completed items are converted to scale scores and to composite scores. These scores are used to determine the child's performance compared with norms taken from typically developing children of their age (in months). The percentile scores between 85 and 115 are usually accepted as normal cognitive development (Black M. M. and Matula K. (1999), Essentials of Bayley Scales of Infant Development II, Assessment, New York: John Wiley, ISBN 978-0-471-32651-9).

Another scale that may be used to measure cognitive function is the Griffiths Scale (Chaudhary T, et al. (2012), Predictive and Concurrent Validity of Standardized Neurodevelopmental Examinations by the Griffiths Scales and Bayley Scales of Infant Development II., Klin Pediatr., December 2012).

The term "synthetic" means obtained by chemical and/or biological means, to the contrary of "natural (found in the nature)".

The term "medium-chain triglycerides" (or MCT) means medium-chain fatty acid esters of glycerol, that is to say a compound formed of a glycerol backbone and three fatty acids, the three fatty acid chains attached to glycerol being medium-chain in length. The medium-chain fatty acids are caproic acid (comprising 6 carbon atoms or C6:0), caprylic acid (comprising 8 carbon atoms or C8:0), capric acid (comprising 10 carbon atoms or C10:0), and lauric acid (comprising 12 carbon atoms or C12:0). The medium-chain fatty acids are mainly (at least 98%) in the form of triglycerides.

The term "long-chain polyunsaturated fatty acid" (or LC-PUFA) means a polyunsaturated fatty acid (PUFA) having C20 or C22 carbon atoms. Polyunsaturated fatty acids (PUFAs) are unsaturated fatty acids that contain more than one double bond in their backbone.

All percentages are by weight of total fat (or lipid) unless otherwise stated.

As used in this specification, the words "comprises", "comprising", and similar words, are not to be interpreted in an exclusive or exhaustive sense. In other words, they are intended to mean "including", but not limited to.

Any reference to prior art documents in this specification is not to be considered an admission that such prior art is widely known or forms part of the common general knowledge in the field.

The composition of the invention is designed to meet the nutritional needs of infants. The composition is aimed to ensure the healthy establishment of a cognitive function in in infants and preferably in preterm infants.

The synthetic nutritional composition of the invention is designed for consumption by infants from birth to one year old. It is specifically designed to meet the nutritional needs of preterm infants.

The composition of the invention contains at least one unsaturated fatty acid, preferably at least one polyunsaturated fatty acid. Among those PUFAs, the composition contains a minor amount (i.e. less than 50 wt %) of LC-PUFA and a major amount (i.e. more than 50 wt %) of unsaturated fatty acids having C18 carbon atoms.

Polyunsaturated fatty acids can be classified in various groups by their chemical structure. Among those PUFAS one may distinguish the omega-3 and omega-6 PUFAs.

Polyunsaturated omega-3 ($\omega$-3 or n-3) fatty acids comprise alpha-linolenic acid (ALA) 18:3, stearidonic acid (SDA) 18:4, eicosatrienoic acid (ETE) 20:3, n-3 eicosatetraenoic acid (ETA) 20:4, eicosapentaenoic acid (EPA) 20:5, n-3 docosapentaenoic acid (DPA) 22:5, and docosahexaenoic acid (DHA) 22:6. Preferably, the PUFAs according to the invention comprise alpha-linolenic acid, which is an essential fatty acid.

Polyunsaturated omega-6 ($\omega$-6 or n-6) fatty acids comprise linoleic acid 18:2, gamma-linolenic acid (GLA) 18:3, n-6 eicosadienoic acid 20:2, dihomo-gamma-linolenic acid (DGLA) 20:3, arachidonic acid (AA or ARA) 20:4, n-6 docosadienoic acid 22:2, and docosapentaenoic acid 22:5. Preferably, the PUFAs according to the invention comprise linoleic acid, which is an essential fatty acid.

Preferably, the unsaturated fatty acids of the composition of the invention further contains at least one LC-PUFA, which is preferably a n-3 and/or a n-6 LC-PUFA (that is to say a n-3 LC-PUFA, a n-6 LC-PUFA or, more preferably, a mixture of n-3 and n-6 LC-PUFA), the LC-PUFA(s) being present in an amount generally of at least 0.8 wt %, preferably at least 1.0 wt %, with respect to the total fatty acids. This leads (taking into consideration that the total fat comprises 90 to 96 wt % of fatty acids, see above) to an amount of at least about 0.8 wt %, preferably at least about 1.0 wt %, with respect to the total fat.

The n-3 LC-PUFA can be a C20 or a C22 n-3 fatty acid. The C20 or C22 n-3 LC-PUFA is preferably present in an amount of at least 0.4 wt %, with respect to all the fatty acids in the composition. This leads to an amount of at least about 0.4 wt %, with respect to the total fat of the composition. Preferably the n-3 LC-PUFA is docosahexanoic acid (DHA, C22:6).

The n-6 LC-PUFA can be a C20 or a C22 n-6 fatty acid. The C20 or C22 n-6 LC-PUFA is preferably present in an amount of at least 0.4 wt % of all fatty acids in the composition.

This leads to an amount of at least 0.4 wt %, with respect to the total fat of the composition. Preferably the n-6 LC-PUFA is arachidonic acid (ARA, C20:4).

Preferably, the LC-PUFAs comprise at least 0.4 wt % of docosahexaneoic acid and at least 0.4 wt % of arachidonic acid, with respect to the total fatty acids.

The source of unsaturated fatty acids may be, for example, egg lipids, fungal oil, low EPA fish oil or algal oil. The LC-PUFA of the composition of the invention may be provided in small amounts of oils containing high quantities of preformed arachidonic acid and docosahexaenoic acid such as fish oils or microbial oils.

The presence of LC-PUFAs is especially advantageous for further improving cognitive benefits, as it is known in the art.

There are many reports in the literature suggesting that these fatty acids may be essential for optimal cognitive function development. Among its many roles, DHA influences the function of the blood-brain barrier, the activity of membrane-bound enzymes and ionic channels, dopaminergic and serotoninergic neurotransmission, and signal transduction (Yaboob, P Annu. Rev. Nutr. 2009.29:257-282).

Preferably the fat of the composition according to the invention are such that it comprises palmitic acid in the form of triglycerides, the palmitic acid being esterified in the sn-2 position of the triglycerides.

The presence of palmitic acid in the form of triglycerides, the palmitic acid being esterified in the sn-2 position of the triglycerides, is especially advantageous for growth benefits, as it is known in the art (Innis S M, Adv Nutr 2011 May 2(3):275-283

According to a particularly preferred embodiment, the composition according to the invention is specially adapted for infants, preferably preterm infants, who were born preterm or with low-birth weight or experienced intrauterine growth retardation or who suffered from growth delays due to disease and/or malnutrition.

The synthetic nutritional composition of the invention may be an infant formula in the form of a powder, liquid or concentrated liquid. The infant formula may be based on a cow's milk, goat's milk or buffalo milk. The infant formula may be a starter formula generally for infants that are less than 6 months old or a follow-on formula generally for infants that are more than 6 months old. The composition of the invention may be a growing up milk, or a human milk fortifier.

The quantities of all the components expressed herein as weight % (wt %) with respect to the total fat, reflect the amounts of some components of the fat present in the synthetic nutritional composition, to be consumed by the infant. For example, the composition may be a powdered infant formula that is diluted with water to give a final liquid product. The composition according to the invention may also be a concentrated liquid that is diluted with water to achieve the final liquid product. The composition of the invention may be a liquid product that is directly consumed by the infant as it is. The composition according to the invention may be a human milk fortifier that is added to or diluted with human milk. In this case, the concentration of the components already present in the human milk (to which the human milk fortifier is added) are to be taken as the average values for lactating mothers that are known or predicted from published clinical data.

The composition according to the present invention contains a source of lipids. The lipid source may be any lipid or fat which is suitable for use in infant formulae, as far as the content of MCFAs in specific proportions and the content of PUFAs meets the requirements of the invention. Preferred fat sources include palm oleic, high oleic sunflower oil and high oleic sunflower oil. The essential fatty acids linoleic and α-linolenic acid may also be added. In the composition, the fat source (including optional LC-PUFA such as ARA and/or DHA) preferably has a ratio of n-6 to n-3 fatty acids of about 1:2 to about 10:1, preferably about 5:1 to about 10:1, even more preferably about 7:1 to about 9:1.

The composition according to the invention is preferably such that the fat consists of a mixture of 38 to 42% of milk fat; 8 to 10% of high oleic sunflower oil; 12 to 16% of sunflower oil, 10 to 14% of canola oil; 7 to 9% of coconut oil; 13 to 17% of an oil comprising 15 to 25 wt %, preferably 17 to 25 wt %, of palmitic acid in the form of triglycerides, 40 to 70 wt %, preferably 50 to 65 wt %, of the palmitic acid being in the sn-2 position of the triglycerides such as Betapol® (from 101 Loders Croklaan); and 1.5 to 2.5% of a mixture of poly-unsaturated fatty acids ARA and DHA (such as a mixture in 1:1 proportion of ARASCO® and DHASCO® from Martek), preferably in a ratio ARA:DHA of about 1:1, with respect to the total fat.

Betapol® could be replaced efficiently by Infat® from AAK/Enzymotec.

Each one of these fat sources is a refined oil suitable for infant nutrition applications.

Other standard ingredients known to the skilled person for formulating an infant formula, human milk fortifier or growing-up milk may also be present in the compositions of the invention.

Thus, the composition of the invention may contain other ingredients which may act to enforce the technical effect of the components, particularly according to the Commission Directive 2006/141/EC of 22 Dec. 2006 on infant formulae and follow-on formulae.

The composition according to the present invention can also contain a carbohydrate source, preferably as prebiotics, or in addition to prebiotics. Any carbohydrate source conventionally found in infant formulae such as lactose, saccharose, maltodextrin, starch and mixtures thereof may be used although the preferred source of carbohydrates is lactose.

The prebiotics that may be used in accordance with the present invention are not particularly limited and include all food substances that promote the growth of probiotics or health beneficial micro-organisms in the intestines. Preferably, they may be selected from the group consisting of oligosaccharides, optionally containing fructose, galactose, and mannose; dietary fibers, in particular soluble fibers, soy fibers; inulin; or mixtures thereof. Preferred prebiotics are fructo-oligosaccharides (FOS), galacto-oligosaccharides (GOS), isomalto-oligosaccharides (IMO), xylo-oligosaccharides (XOS), arabino-xylo oligosaccharides (AXOS), mannan-oligosaccharides (MOS), oligosaccharides of soy, glycosylsucrose (GS), lactosucrose (LS), lactulose (LA), palatinose-oligosaccharides (PAO), malto-oligosaccharides, gums and/or hydrolysates thereof, pectins and/or hydrolysates thereof.

In particular, the human milk oligosaccharides, for example sialylated oligosaccharides, described in WO 2012/069416 published on May 31, 2012 may be included in the composition according to the invention. The latter oligosaccharides may act in synergy with the medium-chain fatty acids of the invention to promote the healthy establishment of cognitive function in the developing infant.

Probiotic may be added to the composition. All probiotic micro-organisms may be added additionally. Preferably, the probiotic may be selected for this purpose from the group consisting of Bifidobacterium, Lactobacillus, Lactococcus, Enterococcus, Streptococcus, Kluyveromyces, Saccharoymces, Candida, in particular selected from the group consisting of Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus lactis, Lactobacillus reuteri, Lactobacillus rhamnosus, Lactobacillus johnsonii, Lactobacillus plantarum, Lactobacillus salivarius, Lactococcus lactis, Enterococcus faecium, Saccharomyces cerevisiae, Saccharomyces boulardii or mixtures thereof, preferably selected from the group consisting of Bifidobacterium longum NCC3001 (ATCC BAA-999), Bifidobacterium longum NCC2705 (CNCM I-2618), Bifidobacterium longum NCC490 (CNCM I-2170), Bifidobacterium lactis NCC2818 (CNCM I-3446), Bifidobacterium breve strain A, Lactobacillus paracasei NCC2461 (CNCM I-2116), Lactobacillus johnsonii NCC533 (CNCM I-1225), Lactobacillus rhamnosus GG (ATCC53103), Lactobacillus rhamnosus NCC4007 (CGMCC 1.3724), Enterococcus faecium SF 68 (NCC2768; NCIMB10415), and mixtures thereof.

The composition according to the invention can also contain a protein source. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions. The proteins can be at least partially hydrolyzed in order to enhancement of oral tolerance to allergens, especially food allergens. In that case the composition is a hypoallergenic composition.

In a preferred embodiment, the composition may be cow's milk whey based infant formula. The formula may also be a hypoallergenic (HA) formula in which the cow milk proteins are (partially or extensively) hydrolysed. The formula may also be based on soy milk or a non-allergenic formula, for example one based on free amino acids.

The composition of the invention can also contain all vitamins and minerals, and other micronutrients, understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the composition of the invention may contain emulsifiers and stabilisers such as soy, lecithin, citric acid esters of mono- and di-glycerides, and the like.

The composition of the invention may also contain other substances which may have a beneficial effect such as lactoferrin, nucleotides, nucleosides, gangliosides, polyamines, and the like.

The preparation of the composition according to the invention will now be described by way of example.

The formula may be prepared in any suitable manner. For example, it may be prepared by blending together a protein source, a carbohydrate source, and a fat source including the MCFAs in appropriate proportions and the PUFAs. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The liquid mixture is then homogenized, for example in two stages.

The liquid mixture may then be thermally treated to reduce bacterial loads, by rapidly heating the liquid mixture to a temperature in the range between about 80° C. and about 150° C. for duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenized, for example in two stages between about 10 MPa and about 30 MPa in the first stage and between about 2 MPa and about 10 MPa in the second stage. The homogenized mixture may then be further cooled to add any heat sensitive components, such as vitamins and minerals. The pH and solids content of the homogenized mixture are conveniently adjusted at this point.

The homogenized mixture is transferred to a suitable drying apparatus such as a spray dryer or freeze dryer and converted to powder. The powder should have a moisture content of less than about 5% by weight. Some of the carbohydrate may be added at this stage by dry-mixing along with optional probiotic bacterial strain(s), or by blending them in a syrup form of crystals, along with optional probiotic bacterial strain(s), and spray-dry (or freeze-dry).

If a liquid composition is preferred, the homogenized mixture may be sterilized then aseptically filled into suitable containers or may be first filled into the containers and then retorted.

In another embodiment, the composition of the invention may be a supplement in an amount sufficient to achieve the desired effect in an infant. This form of administration is usually more suited to preterm infants.

The amount of MCFAs and PUFAs to be included in the supplement will be selected according to the manner in which the supplement is to be administered.

The supplement may be in the form of powder, tablets, capsules, pastilles or a liquid for example, as long as it is a suitable nutritional composition for the infant. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

The supplement can be added in a product acceptable to the consumer (who is an infant), such as an ingestible carrier or support, respectively. Examples of such carriers or supports are a pharmaceutical or a food composition. Examples for such compositions are infant formula including preterm formula.

Further, the supplement may contain an organic or inorganic carrier material suitable for enteral or parenteral administration as well as vitamins, minerals trace elements and other micronutrients in accordance with the recommendations of Government bodies such as the European Commission Directive 2006/141/EC of 22 Dec. 2006 on infant formulae and follow-on formulae.

The composition of the invention is an infant formula (or a follow-on formula or a growing up milk or a human milk fortifier), for infant of less than 12 months, less than 6 months or preferably of 3 months or less. In this case, the composition is a preterm infant formula. It is generally known, or at least hypnotized, that early nutritional interventions can be more effective (in comparison to intervention at later stages in life) in programming the metabolic pathways of the infants to induce optimal balanced growth and thus prevent obesity during infancy and later in life In one embodiment of the invention, the composition of the invention is an infant formula intended and/or especially designed for preterm infants. It is generally known, or at least hypothized, that this subject group is more prone to suffer from unbalanced growth (and, thus, from being obese later in life) due to the immaturity of the metabolic pathways and physiological conditions at birth. Early adaptation and control of the diet is therefore of the highest importance.

In one embodiment of the invention, the composition of the invention is an infant formula (or a follow-on formula or a growing up milk or a human milk fortifier), for infants born from mothers or parents having a history of obesity or overweight. It is generally known, or at least hypothized, that these subjects groups are more prone to suffer from unbalanced growth (and, thus, from being obese later in life), due, for example, to genetic or epi-genetic predispositions. It is, therefore, critical to address such issues as early as possible during infancy by a specifically adapted diet.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention is further described with reference to the following examples. It will be appreciated that the invention as claimed is not intended to be limited in any way by these examples.

Example 1

A mixture of fat was carried out, by the mixing of animal and vegetable fat. Advantageously, on the contrary to the oil mixtures of the prior art infant formulae, this mixture has a MCFAs composition close to a human milk reference data.

The oil mixture composition was the following, with respect to the total fat:
- milk fat: 40%;
- high-oleic sunflower oil: 9%;
- sunflower oil: 14%;
- canola oil: 12%;
- coconut oil: 8%;
- oil mixture of ARA and DHA (ratio 1:1): 2%;
- Betapol® (from IOI Loders Croklaan): 15%.

Betapol® could be replaced efficiently by Infat® from AAK/.

Each of these fat sources is a refined oil suitable for infant nutrition applications.

The lipid composition of this mixture was characterized by two methods as described below.

Determination of triacylglycerols was performed by non-aqueous reversed phase liquid chromatography and hybrid mass spectrometry as recently described in Journal of Lipid Research (2013) volume 54, 290-305. This approach enables the global detection and identification of TAG in their intact form (without chemical derivatization) thus the overview of TAG size distribution is possible and the regioisomeric distribution of various FA including that of P, can be measured simultaneously. Briefly, the identification of the TAG was performed based on the accurate mass and fragmentation pattern obtained by data-dependent fragmentation. The quantitation of TAG was based on the high resolution ion chromatograms, while relative proportion of sn-1(3)/sn-2 regioisomers was calculated based on generalized fragmentation models and the relative intensities observed in the product ion spectra.

Determination of fatty acids was performed by gas chromatography flame ionization detection as described in IUPAC method 2.304, but using methyl-undecanoate as internal standard and a cyanopropylpolysiloxane capillary column. This classical reference approach enables the indirect but most sensitive and most precise quantification of individual (including trans) fatty acids. Briefly, the samples are subjected to transmethylation under alkali conditions resulting in the methyl esters of all fatty acids. The identification and quantification of the individual fatty acid methyl esters is performed based on their chromatographic retention time and peak area respectively.

The total amount of C8:0 to C12:0 fatty acids was 7.7 g/100 g oil.

The total amount of triacylglycerol with the total carbon of the acyl chains between C30 and C36, considered as medium chain triglycerides (MCTs), was 9.5 g/100 g oil.

The sources of the palmitic acidic are as follows, with respect to the total palmitic acid:
- milk fat: 55%;
- high-oleic sunflower oil: 2%;
- sunflower oil: 5%;
- canola oil: 3%;
- coconut oil: 3%;
- oil mixture of ARA and DHA (1:1): 1%;
- Betapol®: 31%.

The total amount of palmitic acid esterified in the sn-1 or sn-3 position was 9.5 g/100 g oil (thus 56% in all palmitic acid).

The total amount of palmitic acid esterified in the sn-2 position was 7.4 g/100 g oil (thus 44% in all palmitic acid).

The total amount of PUFAs was 14.0 g/100 g oil.

The total amount of LC-PUFAs was 0.9 g/100 g oil.

The detailed composition of the oil mixture, with respect to the total fat, was measured as details in Table 1 below.

TABLE 1

Composition of the oil mixture with respect to the total fat

| Name* | Nomenclature | Concentration (g/100 g oil) |
|---|---|---|
| Butyric acid | 4:0 | 1.41 |
| Caproic acid | 6:0 | 1.00 |
| Caprylic acid | 8:0 | 1.10 |
| Capric acid | 10:0 | 1.60 |
| Lauric acid | 12:0 | 4.77 |
| Myristic acid | 14:0 | 5.65 |
| Myristoleic acid | 14:1 n-5 | 0.41 |
| Pentadecanoic acid | 15:0 | 0.46 |
| Palmitic acid | 16:0 | 18.76 |
| Palmitoleic acid | 16:1 n-7 | 0.64 |
| Margaric acid | 17:0 | 0.30 |
| Stearic acid | 18:0 | 4.88 |
| Oleic acid | 18:1 n-9 | 32.17 |
| Linoleic acid (LA) | 18:2 n-6 | 11.48 |
| Alpha-linolenic acid (ALA) | 18:3 n-3 | 1.10 |
| Arachidonic acid (ARA) | 20:4 n-6 | 0.40 |
| Docosahexaenoic acid (DHA) | 22:6 n-3 | 0.40 |

*the MCFAs are in bold and underlined

The detailed composition of the oil mixture, with respect to the total fatty acids, was measured as details in Table 2 below.

TABLE 2

Composition of the oil mixture with respect to the total fatty acids

| Name* | Nomenclature | Concentration (g/100 g oil) |
|---|---|---|
| Butyric acid | 4:0 | 1.56 |
| Caproic acid | 6:0 | 1.11 |
| Caprylic acid | 8:0 | 1.22 |
| Capric acid | 10:0 | 1.77 |
| Lauric acid | 12:0 | 5.27 |
| Myristic acid | 14:0 | 6.25 |
| Myristoleic acid | 14:1 n-5 | 0.45 |
| Pentadecanoic acid | 15:0 | 0.51 |
| Palmitic acid | 16:0 | 20.74 |
| Palmitoleic acid | 16:1 n-7 | 0.71 |
| Margaric acid | 17:0 | 0.33 |
| Stearic acid | 18:0 | 5.40 |
| Oleic acid | 18:1 n-9 | 35.57 |
| Linoleic acid (LA) | 18:2 n-6 | 12.69 |
| Alpha-linolenic acid (ALA) | 18:3 n-3 | 1.22 |
| Arachidonic acid (ARA) | 20:4 n-6 | 0.44 |
| Docosahexaenoic acid (DHA) | 22:6 n-3 | 0.44 |

*the MCFAs are in bold and underlined

This overall fatty acid profile is very close to the fatty acid profile in human milk.

The total amount of PUFAs was 48.4 g/100 g of fatty acids.

The total amount of LC-PUFAs was 0.6 g/100 g of fatty acids.

The n-6/n-3 ratio (weight by weight) of these fatty acids, i.e. the ratio of the n-3 fatty acids to the n-6 fatty acids, was equal to 8.7%.

This oil mixture was mixed with other ingredients so that to provide an infant formula, according to examples 2, 3 and 4 as follows.

Example 2

A first example of a starter infant formula for infants up to the age of three months is given in Table 3 below. The protein source is a conventional mix of whey protein and casein.

TABLE 3

| Nutrient | per 100 kcal | per litre |
|---|---|---|
| Energy (kcal) | 100 | 678 |
| Protein (g) | 1.68 | 11.3 |
| Oil mixture of example 1 (g) | 6.38 | 43.64 |
| Lactose (g) | 9.41 | 62.6 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1 |
| Niacin (mg) | 1 | 6.7 |
| Vitamin B6 (mg) | 0.075 | 0.5 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |

Example 3

A second example of a starter infant formula for infants up to the age of three months is given in Table 4 below. The protein source is a conventional mix of whey protein and casein.

TABLE 4

| Nutrient | per 100 kcal | per litre |
|---|---|---|
| Energy (kcal) | 100 | 640.4 |
| Protein (g) | 1.66 | 10.72 |
| Oil mixture of example 1 (g) | 6.18 | 39.8 |
| Lactose (g) | 9.98 | 62.88 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |

TABLE 4-continued

| Nutrient | per 100 kcal | per litre |
|---|---|---|
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1 |
| Niacin (mg) | 1 | 6.7 |
| Vitamin B6 (mg) | 0.075 | 0.5 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |

Example 4

An example of an infant formula for infants older than three months is given in Table 5 below. The protein source is a conventional mix of whey protein and casein.

TABLE 5

| Nutrient | per 100 kcal | per litre |
|---|---|---|
| Energy (kcal) | 100 | 775.64 |
| Protein (g) | 1.18 | 8.48 |
| Oil mixture of example 1 (g) | 6.73 | 53.88 |
| Lactose (g) | 8.64 | 63.56 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1 |
| Niacin (mg) | 1 | 6.7 |
| Vitamin B6 (mg) | 0.075 | 0.5 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |

The invention claimed is:

1. A method for promoting the healthy establishment of cognitive function in an infant comprising administering to the infant a synthetic infant formula composition comprising medium-chain fatty acids, in the form of triglycerides, in a total amount in the range of 2.0 to 10.0 wt %, caproic acid in an amount in the range of 0.6 to 1.3 wt % with respect to the total fat, caprylic acid in an amount in the range of 0.8 to 1.5 wt % with respect to the total fat, capric acid in the amount in the range of 1.4 to 1.9 wt % with respect to the total fat, lauric acid in an amount in the range of 4.0 to 6.0 wt % with respect to the total fat, and at least one unsaturated fatty acid, the at least one unsaturated fatty acid being present in an amount of at least 15 wt % with respect to the total fatty acids.

2. The method of claim 1, wherein the infant is a preterm infant.

3. The method of claim 1, wherein the infant was born preterm or with low-birth weight or experienced intra-uterine growth retardation or suffered from growth delays due to disease and/or malnutrition.

4. The method of claim 1, wherein the composition comprises:
  0.7 to 1.1 wt. % of the caproic acid;
  0.9 to 1.2 wt. % of the caprylic acid;
  1.5 to 1.8 wt. % of the capric acid; and
  4.5 to 5.9 wt. % of the lauric acid.

5. The method of claim 1, wherein the composition comprises:
  0.8 to 1.0 wt. % of the caproic acid;
  1.0 to 1.1 wt. % of the caprylic acid;
  1.6 to 1.7 wt. % of the capric acid; and
  4.5 to 5.5 wt. % of the lauric acid.

6. The method of claim 1, wherein the fat consists of a mixture of 38 to 42 wt. % of milk fat; 8 to 10 wt. % of high oleic sunflower oil; 12 to 16 wt. % of sunflower oil; 10 to 14 wt. % of canola oil; 7 to 9 wt. % of coconut oil; 13 to 17 wt. % of an oil comprising 15 to 25 wt. % of palmitic acid in the form of triglycerides, 40 to 70 wt. % of the palmitic acid being in the sn-2 position of the triglycerides; and 1.5 to 2.5 wt. % of a mixture of poly-unsaturated fatty acids ARA and DHA, each with respect to the total fat.

7. The method of claim 1, wherein the at least one unsaturated fatty acid of the composition comprises a long-chain polyunsaturated fatty acid (LC-PUFA), and the at least one LC-PUFA is at least 1.0 wt. % with respect to the total fatty acids.

8. The method of claim 7, wherein the at least one LC-PUFA comprises at least 0.4 wt. % of docosahexaneoic acid and at least 0.4 wt. % of arachidonic acid, with respect to the total fatty acids.

9. The method of claim 7, wherein the at least one LC-PUFA comprises palmitic acid in the form of triglyceride, and the palmitic acid is esterified in the sn-2 position of the triglyceride.

* * * * *